(12) United States Patent
Falwell et al.

(10) Patent No.: US 7,604,611 B2
(45) Date of Patent: Oct. 20, 2009

(54) HANDLE THUMB WHEEL MECHANISM WHICH MAINTAINS HOLDING FORCES WHEN STERILIZED AND WHEN ENGAGED

(75) Inventors: Gary S. Falwell, Wilmington, MA (US); Steven J. Burns, Haverhill, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 202 days.

(21) Appl. No.: 10/488,856

(22) PCT Filed: Oct. 21, 2002

(86) PCT No.: PCT/US02/33609

§ 371 (c)(1),
(2), (4) Date: Aug. 9, 2006

(87) PCT Pub. No.: WO03/033064

PCT Pub. Date: Apr. 24, 2003

(65) Prior Publication Data

US 2007/0032759 A1    Feb. 8, 2007

Related U.S. Application Data

(60) Provisional application No. 60/345,119, filed on Oct. 19, 2001.

(51) Int. Cl.
| | |
|---|---|
| *A61M 37/00* | (2006.01) |
| *A61M 31/00* | (2006.01) |
| *A61B 18/18* | (2006.01) |
| *A61B 1/00* | (2006.01) |

(52) U.S. Cl. ............... 604/95.04; 606/41; 600/148

(58) Field of Classification Search ............... D27/154, D27/156, 158; 604/280, 95.04, 95.01; 446/23, 446/288, 330, 334, 22; 81/58, 62, 63.1, 63.2; 227/179.1; 474/80, 82; 74/480 R, 526, 551.8; 248/279.1

See application file for complete search history.

(56) References Cited

U.S. PATENT DOCUMENTS

| 4,527,023 A | * | 7/1985 | Ohashi et al. | ............ 200/11 G |
| 4,733,034 A | * | 3/1988 | Armstrong et al. | .......... 200/564 |

(Continued)

FOREIGN PATENT DOCUMENTS

EP        0616794        9/1994

(Continued)

OTHER PUBLICATIONS

European Communication Pursuant to Article 96(2) EPC, dated Oct. 27, 2005.

*Primary Examiner*—Nicholas D Lucchesi
*Assistant Examiner*—Ian K Holloway
(74) *Attorney, Agent, or Firm*—Leason Ellis LLP

(57) ABSTRACT

A thumb wheel mechanism includes a thumb wheel with upper and lower surfaces, the lower surface including a bore with a ball connected to it, and an handle half with upper and lower surfaces, the upper surface including a divot, the thumb wheel lower surface being aligned with the handle half upper surface so that the ball rests in the divot of the handle half upper surface when the thumb wheel mechanism is in the neutral position, thereby minimizing the compression load on the thumb wheel mechanism.

15 Claims, 4 Drawing Sheets

U.S. PATENT DOCUMENTS

| | | | |
|---|---|---|---|
| 5,327,906 | A | 7/1994 | Fideler |
| 5,395,329 | A | 3/1995 | Fleischhacker et al. |
| 5,397,321 | A | 3/1995 | Houser et al. |
| 5,423,771 | A | 6/1995 | Imran |
| 5,462,527 | A | 10/1995 | Stevens-Wright et al. |
| 5,575,755 | A * | 11/1996 | Krauter et al. ............... 600/148 |
| 5,611,777 | A | 3/1997 | Bowden et al. |
| 5,904,667 | A | 5/1999 | Falwell |
| 6,797,907 | B1 * | 9/2004 | Meagher et al. ............. 200/564 |
| 7,331,958 | B2 * | 2/2008 | Falwell et al. .................. 606/41 |
| 2004/0193239 | A1 * | 9/2004 | Falwell et al. ............... 607/122 |
| 2006/0241366 | A1 * | 10/2006 | Falwell et al. ............... 600/374 |

FOREIGN PATENT DOCUMENTS

| | | |
|---|---|---|
| EP | 0605796 | 8/2003 |
| WO | WO-94/11057 | 5/1994 |
| WO | WO-02/087455 | 11/2002 |
| WO | WO-02/087676 | 11/2002 |

* cited by examiner

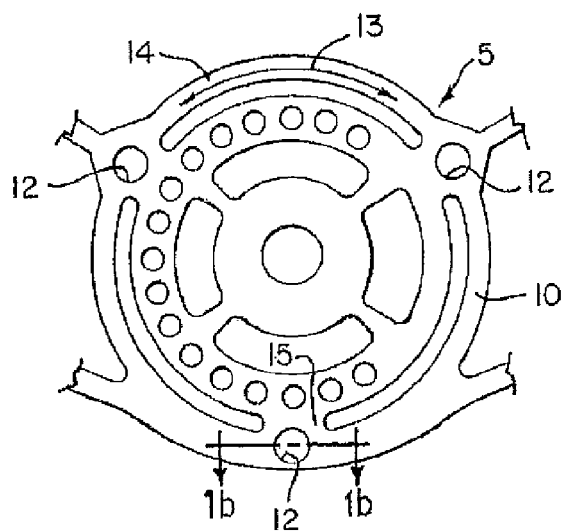
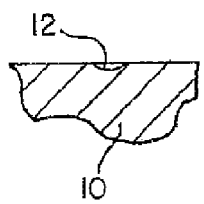
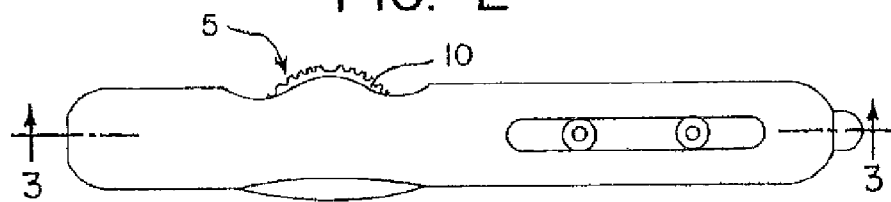
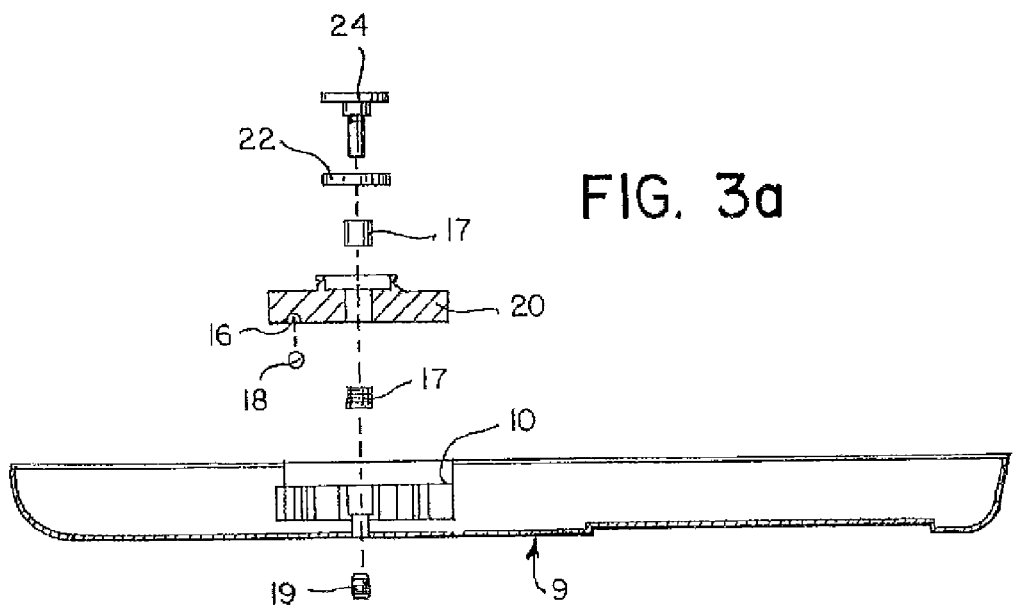

HANDLE THUMB WHEEL MECHANISM WHICH MAINTAINS HOLDING FORCES WHEN STERILIZED AND WHEN ENGAGED

FIELD OF THE INVENTION

This invention relates to a thumb wheel mechanism for a deflectable tip catheter. More particularly, this invention relates to a thumb wheel mechanism with a minimized compression force in a neutral position and a locking frictional force in an engaged position.

BACKGROUND OF THE INVENTION

A two dimensional/three dimensional steerable catheter can deflect four pull cables, generating curves in four different planes. Currently, this is accomplished by having a distal tip segment that can be deflected into four independent quadrants using separate pull cables attached to a distal tip. The four pull cables are controlled by two independent mechanisms. One of the mechanisms consists of a thumb wheel that, when rotated both in a clockwise and a counterclockwise direction from a neutral position, generates tension to two of the four independent cables. The second mechanism utilizes a slider control, which when slid forward and backward from a neutral position, generates tension to the remaining two independent cables. The construction and operation of the thumb wheel mechanism is further described in U.S. Pat. No. 5,611,777 to Bowden, Russel W., Falwell, Gary S. et al, issued Mar. 18, 1997 and U.S. Pat. No. 5,904,667 to Falwell, issued May 18, 1999, each of these patents is hereby incorporated by reference in its entirety. After the user actuates either of the handle mechanisms, it is desired that the degree of deflection be maintained until actively changed by the user. Therefore, each of the mechanisms must generate a frictional holding force which is larger than the unloading force of a fully actuated curve.

However, the frictional holding force has been found to significantly decrease after the materials which make up the mechanism are exposed to 65° C. during the sterilization cycle. The reason for this degradation in holding force is that residual stresses are introduced during the assembly of the handle. These stresses appear to be close to the yield strength of the materials used within the assembly at ambient temperatures. When the materials are exposed to an elevated temperature, they experience a decrease in modulus, causing the materials to yield within the assembly resulting in a decrease in holding force.

SUMMARY OF THE INVENTION

The thumb wheel mechanism is exposed to elevated temperatures when it is in neutral position during sterilization. By reducing the stress on the mechanism while in neutral position, this invention minimizes the amount of stress to the thumb wheel mechanism while it is exposed to an elevated temperature during sterilization. This is accomplished by applying a minimal compression load to the thumb wheel mechanism in neutral position.

DESCRIPTION OF THE DRAWINGS

FIG. 1a is a top view of a handle half of the thumb wheel mechanism according to an embodiment of the present invention;

FIG. 1b is a sectional side view of a divot in the handle half of FIG. 1a along line 1b-1b according to an embodiment of the present invention;

FIG. 2 is a top view of the thumb wheel mechanism according to an embodiment of the present invention;

FIG. 3a is an exploded side sectional view of the thumb wheel mechanism of FIG. 2 along line 3-3 according to an embodiment of the present invention;

DETAILED DESCRIPTION OF EXEMPLARY EMBODIMENTS

Figure 3B:
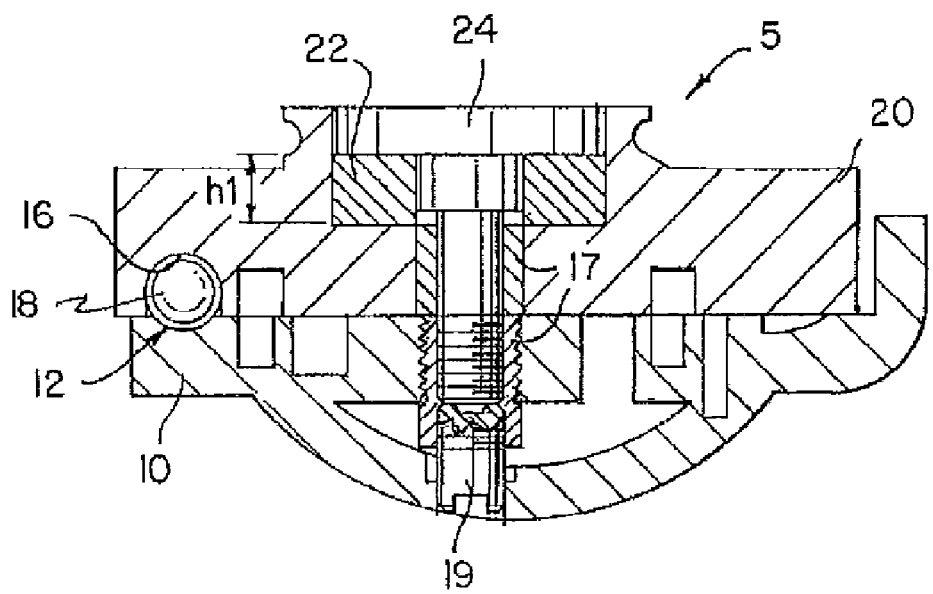
FIG. 3b is a side section view of the thumb wheel mechanism of FIG. 2 along line 3-3 with one of the balls nested into the base of the handle half according to an embodiment of the present invention.

As shown in FIGS. 1a, 1b, 3a, 3b and 3c, one embodiment of the invention consists of thumb wheel mechanism 5 as follows: a handle half bolt circle 10 with three equally spaced full radius divots 12. Three equally spaced counter bores 16 on a thumb wheel 20 (as shown in FIG. 3a) to the handle half 10 are positioned on the thumb wheel 20. Three stainless steel balls 18 are pressed into each of the three counter bores 16 in the thumb wheel 20. The balls 18 can also be constructed from plastic, such as a polymer, nylon, Delrin® (manufactured by Hi-Tech Profiles, Inc., Pawcatuck, Conn.) and ABS® (manufactured by Hi-Tech Profiles, Inc., Pawcatuck, Conn.). The balls 18 either are nested into the base of the divots 12 or ride just outside the divots 12 on a level surface 15 of the handle half 10 along an arcuate path indicated as 13 in FIG. 1a. A friction disk 22 is inserted under the head of a shoulder screw 24. The shoulder screw 24 and passes through the thumb wheel 20 acting as an axial and is screwed to the handle half 10. Varying the depth of the shoulder screw 24 controls the compression rate of the friction disk 22. When the thumb wheel mechanism 5 is assembled and placed in the neutral position, all three balls 18 are nested into the base of the divots 12. In this position, the friction disk 22 is under minimal compression. This enables the thumb wheel mechanism 5 to be under minimal stresses in neutral position. Since all sterilization and aging is performed with the thumb wheel mechanism 5 in neutral position, this results in little to no change in holding force post sterilization and aging. As the thumb wheel 20 is rotated, the three balls 18 ride out of the divots 12 on surface 15 and thereby increase the compression forces on the friction disk 22. FIG. 1b is a sectional side view of a divot in the handle half of FIG. 1a along line 1b-1b according to an embodiment of the present invention.

One advantage of the illustrated embodiment of the present invention is that the thumb wheel mechanism 5 can be rotated to hold a curve in the catheter which it controls without requiring a separate locking device. Also, the illustrated embodiment is able to maintain constant friction after it has been exposed to elevated temperatures and overcomes problems with material creep commonly associated with plastic components in a compression state under elevated temperatures. The balls 18 and divots 12 of the illustrated embodiment also provide tactile detents which indicate to the user that the thumb wheel mechanism 5 is in neutral position. Furthermore, the illustrated embodiment enables the thumb wheel mechanism 5 to maintain its set force after it has been through repeated temperature cycles. This provides an advantage if a catheter is subjected to repeated sterilization cycles required for re-processing or re-use. The illustrated embodiment also enables handle holding forces to be easily set in manufacturing.

FIG. 2 is a top view of the thumb wheel mechanism 5 according to an embodiment of the present invention, including a portion of the thumb wheel 20 protruding outside the handle of the catheter. FIG. 3a is an exploded side sectional view of the thumb wheel mechanism 5 of FIG. 2 along line 3-3 according to an embodiment of the present invention. The thumb wheel mechanism 5 is shown, including the thumb wheel 20 with a bore 16 and the handle half 10 with a divot 12. Also shown is the shoulder screw 24, the friction disk 22 located as assembled under the head of the shoulder screw 24 and threaded inserts 17 and set screw 19. The inserts 17 and 19 secure the shoulder screw 24 as an axial through the thumb wheel 20 and attach the screw 24 to the handle half 10.

FIG. 3b is a side section view of the thumb wheel mechanism of FIG. 2 along line 3-3 with one of the balls 18 nested into the base of the handle half 10 according to an embodiment of the present invention. Also shown is the relationship between the shoulder screw 24, the friction disk 22 and the threaded inserts 17 and set screw 19 as assembled. The positioning of the balls 18 nested into the divots 12 when the thumb wheel 20 is in neutral position results in a height $h_1$ of the friction disk 22. Also in this embodiment, the thumb wheel 20 contacts the handle half 10. In alternative embroilments, the thumb wheel 20 need not contact the handle half 10, such as when the diameter of the balls 18 is greater than the combination of depths of the bores 16 and their corresponding divots 12.

Figure 3C:
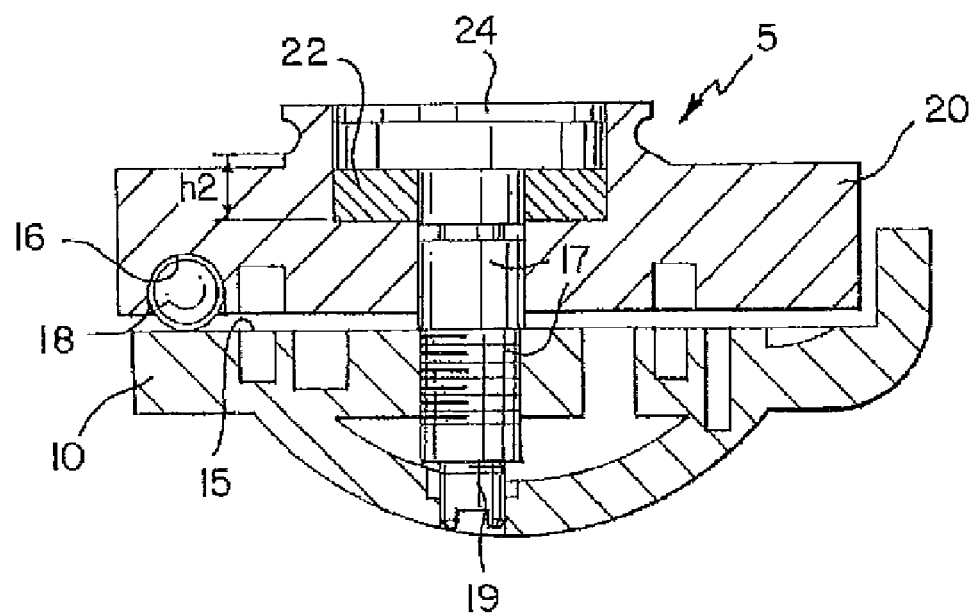
FIG. 3c is a side section view of the thumb wheel mechanism of FIG. 2 along line 3-3 with one of the balls located on the level surface outside one of the divots on the handle half according to an embodiment of the present invention.

FIG. 3c is a side section view of the thumb wheel mechanism 5 of FIG. 2 along line 3-3 with one of the balls 18 located on the level surface 15 outside of the divots 12 on the handle half 10 according to an embodiment of the present invention. The positioning of the balls 18 on the level surface 15 outside the divots 12 when the thumb wheel 20 is engaged results in an upward force on the friction disk 22. Therefore, the friction disk 22 is compressed to a height $h_2$, where $h_2$ is less than $h_1$. An example of the dimensions of the FIGS. 3a, 3b and 3c embodiment is as follows: the diameter of the balls 18 is 0.125 inches; the depth of the bores 16 is 0.01 inches; the depth of the divots 12 is 0.018 inches; the height $h_1$ of the friction disk 22 with the thumb wheel 20 in neutral position is 0.100 inches; the height $h_2$ of the friction disk 22 with the thumb wheel 20 engaged is 0.82 inches.

Figure 4A:
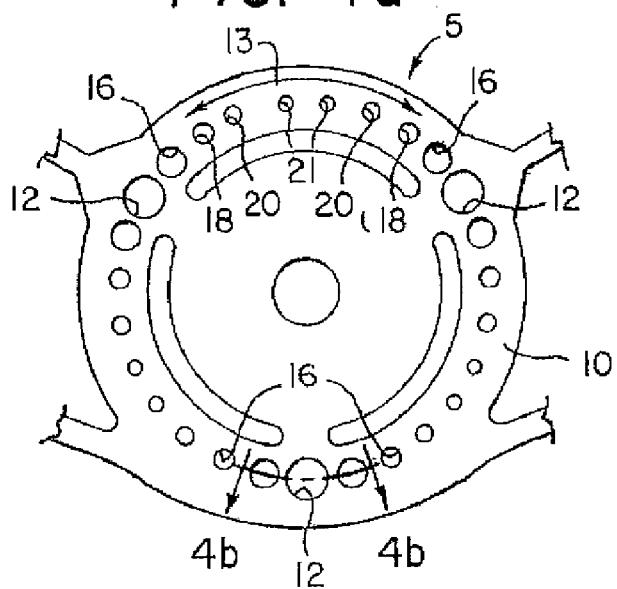
FIG. 4a is a top view of a handle half of the thumb wheel mechanism including multiple divots of varying depths with divots having a maximum depth surrounding the divots corresponding to a neutral position of the thumb wheel according to an alternative embodiment of the present invention.

FIG. 4a is a top view of an alternative embodiment of the handle half 10 with additional divots 16, 18, 20, 21 and 23. The additional divots 16, 18, 20, 21, and 23 are located on the arcuate path 13 followed by the balls 18 between divots 12. Divots 12 correspond to the placement of balls 18 in the neutral position of the thumb wheel 20. It has been determined that the force on the thumb wheel 20 as the thumb wheel 20 is engaged to tension a cable into a curve is inversely proportional to the compression load on the friction disk 22 and the relationship is generally linear. Therefore, as the thumb wheel 20 is engaged to relocate the balls 18 out of the divots 12 to the surface 15 defined by the path 13, there is a retention force at each point necessary to maintain the curvature of the cable. The transition from the depth of the divots 12 to the level surface 15 defined by the path 13 without further depressions (for example, as shown in FIGS. 1a and 1b) can exceed the retention force required to maintain the curvature of the cable at points along path 13. In this embodiment, the additional divots 16, 18, 20, 21 and 23 provide varying depths (for example, a maximum depth for divots 16 to a minimum depth for divots 23) which still provide the required retention force but also provide additional tactile indents to enable the user to optimize control of rotation of the thumb wheel 20 in relation to the curvature achieved. More particularly, the maximum depth is less than the depth of divots 12 which provide a neutral position of thumb wheel 20. For example, the depth of divots 12 is 0.018 inches; the depth of divots 16 is 0.012 inches; the depth of divots 18 is 0.008 inches; the depth of divots 20 is 0.006 inches; the depth of divots 21 is 0.004 inches; and, the depth of divots 23 is 0.002 inches. In an alternative embodiment, the depth of each of divots 16, 18, 20, 21 and 23 can be equal and can provide a retention force for maintaining the curvature of the cable achieved by rotating the thumb wheel 20.

Figure 4B:
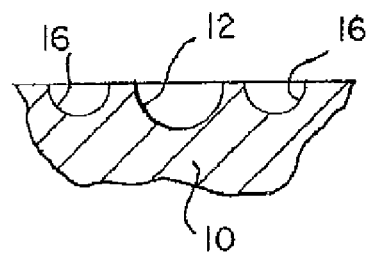
FIG. 4b is a sectional side view of a portion of the divots in the handle half of FIG. 4a along line 4b-4b according to an alternative embodiment of the present invention.

FIG. 4b is a sectional side new of FIG. 4a along line 4b-4b including a cross section of divots 12 and 14. The variation in the depth of divots 12 and 14 is illustrated with the divots 12 depth being greater than the divots 14 depth.

Figure 5A:
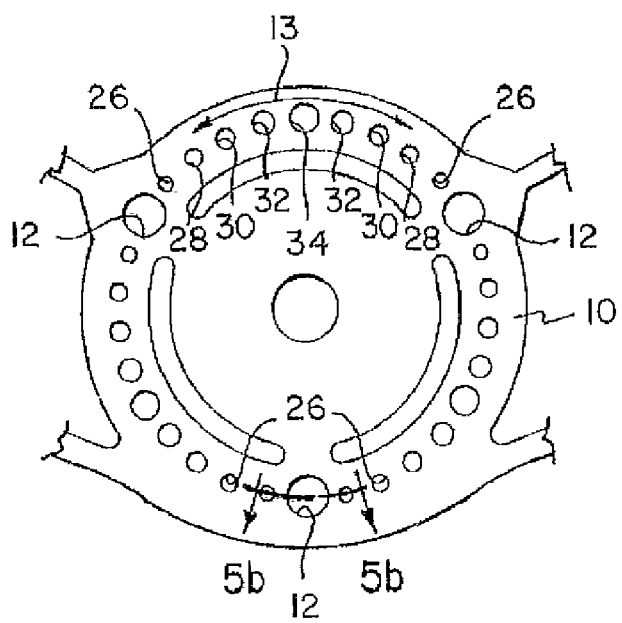
FIG. 5a is a top view of a handle half of the thumb wheel mechanism including multiple divots of varying depths with divots having a minimum depth surrounding the divots corresponding to a neutral position of the thumb wheel according to an alternative embodiment of the present invention.

A further alternative embodiment is shown in FIG. 5a as a top view of a handle half 10 with additional divots 26, 28, 30, 32 and 34. The additional divots serve the same purpose as the FIG. 4a divots, however, in this embodiment, the divots vary from a minimal depth for divots 26 to a maximum depth for divots 34. For example the depth of divots 12 is 0.018 inches; the depth of divots 26 is 0.002 inches; the depth of divots 28 is 0.005 inches; the depth of divots 30 0.008 inches; the depth of divots 32 is 0.012 inches; and, the depth of divots 34 is 0.016 inches.

Figure 5B:
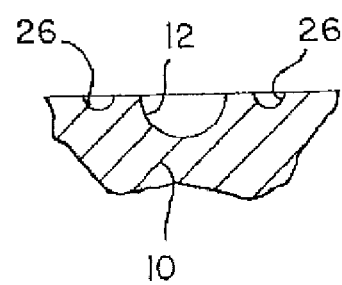
FIG. 5b is a sectional side view of a portion of the divots in the handle half of FIG. 5a along line 5b-5b according to an alternative embodiment of the present invention.

FIG. 5b is a sectional side view of FIG. 5a along line 5b-5b including a cross section of divots 12 and 26. The variation in the depth of divots 12 and 26 is illustrated with the divot 12 depth being greater than the divot 26 depth.

Figure 6A:
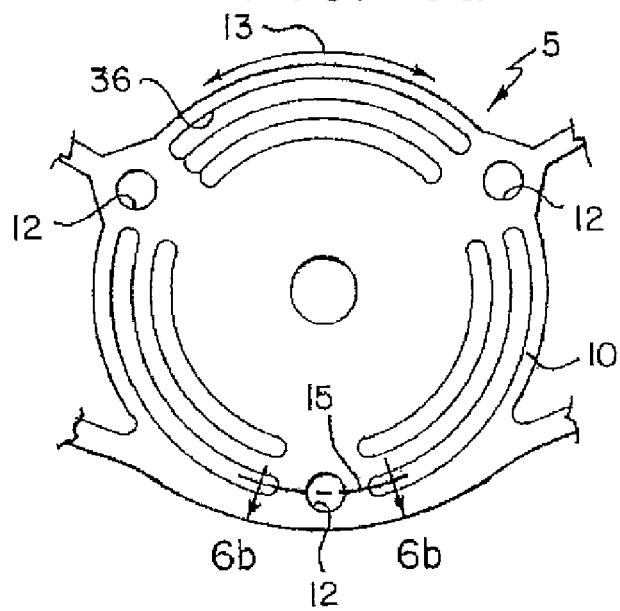
FIG. 6a is a top view of a handle half of the thumb wheel mechanism including a divot ramp with a continuum of varying depths according to an alternative embodiment of the present invention.

FIG. 6a provides a further alternative embodiment based on a top view of handle half 10 with ramped divots 36. The ramp divots 36 are located on the arcuate path 13 between each of the divots 12 along which the balls 18 move. There is a level surface 15 in between the divots 12 and the ramp divots 36. The ramp divots 36 provide a varying depth from a minimum depth closest to divots 12 to a maximum depth at a point equidistant from two divots 12 along the arcuate path 13 (i.e., the location of divots 34 in FIG. 5a) In an alternative embodiment, the ramp can be oriented with a maximum depth closest to the divots 12 and a minimum depth at a point equidistant from two divots 12. The ramp 36 can also include an undulating shape, tooth patterns or any other shape where the maximum depth is less than the depth of divots 12.

Figure 6B:
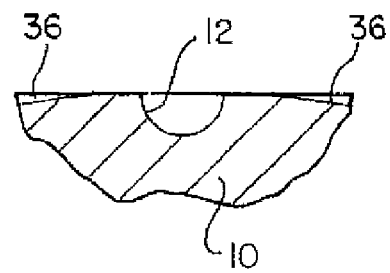
FIG. 6b is a sectional side view of a portion of the divots in the handle half of FIG. 6a along line 6b-6b according to an alternative embodiment of the present invention.

FIG. 6b is a sectional side view of FIG. 6a along line 6b-6b including a cross section of divots 12 and ramp divots 36. There is a level surface 15 in between divots 12 and 36 and the maximum depth of divot 36 is less than the depth of divot 12.

Figure 7A:
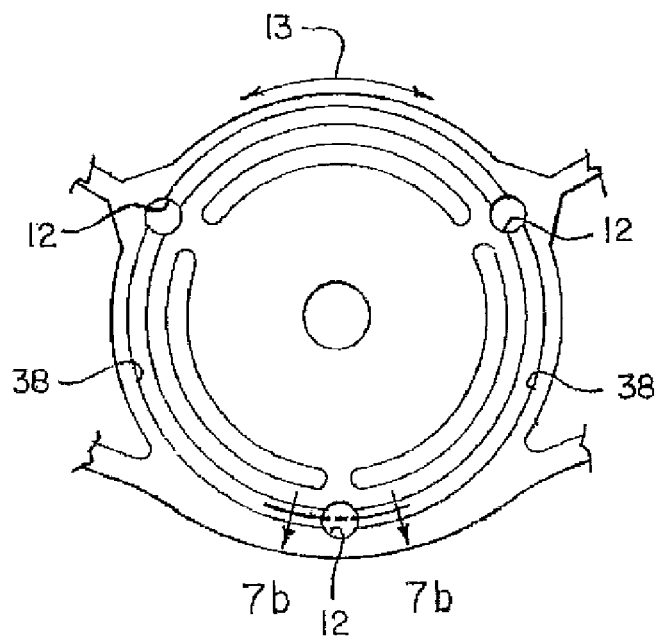
FIG. 7a is a top view of a handle half of the thumb wheel mechanism including a divot ramp with a continuum of varying depths connected to the divots according to an alternative embodiment of the present invention.

FIG. 7a provides a further alternative embodiment based on a top view of handle half 10 with ramped divots 38. In this embodiment the ramped divots abut divots 12 at the maximum depth of divots 38 then divots 38 incline to a minimum depth at a point equidistant from divots 12 along the arcuate path 13.

Figure 7B:
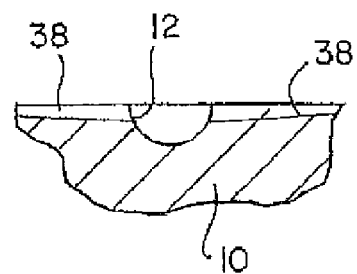
FIG. 7b is a sectional side view of a portion of the divots in the handle half of FIG. 7a along line 7b-7b according to an alternative embodiment of the present invention.

FIG. 7b is a sectional side view of FIG. 7a along line 7b-7b including a cross section of divots 12 and ramp divots 38, showing the connection of divots 12 and ramp 38. The maximum depth of divots 36 is less than the depth of divots 12.

We claim:

1. A thumb wheel mechanism for use with a deflectable tip catheter with reduced stress in neutral position, the thumb wheel mechanism comprising:
   a thumb wheel having a first upper surface opposing a first lower surface, the first lower surface including a bore and a ball connected to the bore, the ball having a diameter greater than the depth of the bore;
   a handle half having a second upper surface opposing a second lower surface, the second upper surface including a divot, the first lower surface being positioned over the second upper surface and the divot being aligned with the bore so that when the thumb wheel is in a neutral position, a portion of the ball extending beyond the first lower surface rests in the divot; and
   the thumb wheel further comprising a friction disk, whereby when the thumb wheel is in the neutral position, a minimal compression load is applied to the friction disk due to the location of the ball in the divot and conversely when the thumb wheel is in an engaged position and the ball rests along the second upper surface outside the divot, a force is applied on the friction disk resulting in compression thereof.

2. The thumb wheel mechanism of claim 1 further comprising the first lower surface including a plurality of equally spaced bores, each of the bores having a ball, and the second upper surface including plurality of equally spaced divots, each of the bores being aligned with one of the divots and the balls resting in the divots when the thumb wheel mechanism is in the neutral position.

3. The thumb wheel mechanism of claim 1 wherein the ball is comprised of one of steel, a plastic, a polymer, and a nylon.

4. The thumb wheel mechanism of claim 1 wherein the thumb wheel and the handle half are comprised of one of a plastic, a polymer, and a nylon.

5. The thumb wheel mechanism of claim 1 further comprising:
   a shoulder screw being positioned as an axial through the thumb wheel and attached to the handle half; and
   the friction disk being inserted under the head of the shoulder screw whereby when the thumb wheel is in the neutral position with the ball resting in the divot, the shoulder screw is minimally engaged so that a minimal compression load is applied to the friction disk.

6. A thumb wheel mechanism for use with a deflectable tip catheter, the catheter including a deflectable cable, the thumb wheel mechanism for further tensioning the cable into a curve and including a locking frictional force when engaged, the thumb wheel mechanism comprising:
   a thumb wheel having a first upper surface opposing a first lower surface, the first lower surface including a bore and ball connected to the bore, the ball having a diameter greater than the depth of the bore;
   a handle half having a second upper surface opposing a second lower surface, the second upper surface including a divot and a level surface around the divot, the first lower surface being positioned over the second upper surface and the divot being aligned with the bore so that when the thumb wheel is engaged by rotation in one of the clockwise and counterclockwise directions, a portion of the ball extending beyond the first lower surface rides outside the divot onto the level surface around the divot; and
   the thumb wheel further comprising a friction disk formed of a compressible material and disposed along the first upper surface whereby when the thumb wheel is engaged, a compression load is applied to the friction disk which is larger than the unloading force of the cable in a fully actuated curve to lock the thumb wheel mechanism.

7. The thumb wheel mechanism of claim 1 further comprising the first lower surface including a plurality of equally spaced bores, each of the bores having a ball, and the second upper surface including a plurality of equally spaced divots and a level surface surrounding each of the divots, each of the bores being aligned with one of the divots and the balls riding outside the divots onto the level surfaces around the divots when the thumb wheel is engaged.

8. The thumb wheel mechanism of claim 6 wherein the balls are comprised of one of steel, a plastic, a polymer, and a nylon.

9. The thumb wheel mechanism of claim 6 wherein the thumb wheel and handle half are comprised of one of a plastic, a polymer, and a nylon.

10. The thumb wheel mechanism of claim 6 further comprising:
    a shoulder screw being positioned as an axial through the thumb wheel and attached to the handle half; and
    the friction disk being inserted under the head of the shoulder screw whereby when the thumb wheel is engaged with the ball in contact with the level surface surrounding the divot, the shoulders screw is engaged so that a friction force greater than the unloading force of the cable of a fully actuated curve is applied to the friction disk.

11. A thumb wheel mechanism for use with a deflectable tip catheter, the catheter including a deflectable cable, the thumb wheel mechanism for further tensioning a cable into a curve and including a plurality of locking positions, each locking position corresponding to a frictional force, the thumb wheel mechanism comprising: a thumb wheel having a first upper surface opposing a first lower surface, the first lower surface including a bore and a ball connected to the bore, the ball having a diameter greater than the depth of the bore; a handle half having a second upper surface opposing a second lower surface, the second upper surface including a divot having a first predetermined depth, a level surface around the divot, and a depression having a second predetermined depth, the first predetermined depth being greater than the second predetermined depth, the first lower surface being positioned over the second upper surface and the divot being aligned with the bore so that when the thumb wheel is engaged by rotation in one of clockwise and counterclockwise directions, a portion of the ball extending beyond the first lower surface rides outside the divot surface onto one of the level surface and the depression; and the thumb wheel further comprising a friction disk formed of a compressible material, the friction disk being in contact with the first upper surface, whereby when the thumb wheel is engaged so that the ball is aligned with the depression, a compression load is applied to the friction disk which is larger than the unloading force cable in a fully activated curve to lock the thumb wheel mechanism.

12. The thumb wheel mechanism of claim 11 wherein the compression load applied to the friction disk when the ball is aligned with the depression is different than the compression load applied to the friction disk when the ball is aligned with the level surface around the divot.

13. The thumb wheel mechanism of claim 11 further comprising a plurality of depressions, with at least two of the depressions having varying predetermined depths to thereby provide different compression loads.

14. The thumb wheel mechanism of claim 1, wherein the depression comprises one of an incline and a decline to provide a continuum of different compression loads.

15. A method of operating a thumb wheel mechanism for use with a deflectable tip catheter, the catheter including a deflectable cable, the thumb wheel mechanism for further tensioning a cable into a curve and including a locking frictional force, the thumb wheel mechanism including a thumb wheel having a first upper surface opposing a first lower surface, the first lower surface including a bore and ball connected to the bore, the ball having a diameter greater than the depth of the bore, a handle half having a second upper surface opposing a second lower surface, the second upper surface including a divot and a level surface around the divot, the first lower surface being positioned over the second upper surface and the divot being aligned with the bore, the thumb wheel further including a friction disk formed of a compressible material and located along the first upper surface, the method comprising: rotating the thumb wheel one of clockwise and counterclockwise so that a portion of the ball extending beyond the first lower surface rides outside the divot onto the level surface around the divot; and the friction disk being compressed with a compression load that is directed toward the thumb wheel and which is larger than the unloading force of the cable in a fully actuated curve to lock the thumb wheel mechanism.

* * * * *